(12) United States Patent
Garcia

(10) Patent No.: US 9,572,752 B1
(45) Date of Patent: Feb. 21, 2017

(54) MEDICAL PORT ASSEMBLY

(71) Applicant: Yvonne Garcia, Miami, FL (US)

(72) Inventor: Yvonne Garcia, Miami, FL (US)

(*) Notice: Subject to any disclaimer, the term of this patent is extended or adjusted under 35 U.S.C. 154(b) by 72 days.

(21) Appl. No.: 14/789,336

(22) Filed: Jul. 1, 2015

(51) Int. Cl.
*A61J 15/00* (2006.01)
*A61M 25/02* (2006.01)

(52) U.S. Cl.
CPC ......... *A61J 15/0053* (2013.01); *A61J 15/0069* (2013.01); *A61M 25/02* (2013.01); *A61M 2025/0246* (2013.01); *A61M 2025/0266* (2013.01)

(58) Field of Classification Search
CPC ............. A61M 2025/0246; A61M 2025/0266; A61M 2025/0273; A61M 25/02; A61J 15/0069; A61J 15/0053
See application file for complete search history.

(56) References Cited

U.S. PATENT DOCUMENTS

| | | | | | |
|---|---|---|---|---|---|
| 3,422,817 A | * | 1/1969 | Mishkin | .............. | A61M 16/047 128/207.14 |
| 3,926,182 A | * | 12/1975 | Stabholz | .................. | A61F 5/024 602/19 |
| 4,074,397 A | * | 2/1978 | Rosin | ..................... | A61M 25/02 128/DIG. 15 |
| 4,089,331 A | * | 5/1978 | Hartigan | ................. | A61B 46/00 128/850 |
| 4,221,215 A | * | 9/1980 | Mandelbaum | ...... | A61M 16/047 128/DIG. 26 |
| 4,323,062 A | * | 4/1982 | Canty | ................... | A61M 25/02 128/852 |
| 4,666,432 A | * | 5/1987 | McNeish | .............. | A61M 25/02 128/DIG. 26 |
| 4,685,901 A | * | 8/1987 | Parks | .................. | A61J 15/0015 604/103.03 |
| 4,799,923 A | * | 1/1989 | Campbell | ............. | A61M 25/02 128/DIG. 26 |
| 5,304,145 A | * | 4/1994 | Blair | ..................... | A61M 25/02 128/DIG. 6 |
| 5,354,261 A | * | 10/1994 | Clark | .................... | A61F 15/004 128/854 |
| 5,918,599 A | * | 7/1999 | Shesol | ............. | A61M 16/0465 128/207.17 |
| 6,267,115 B1 | * | 7/2001 | Marshel | ................ | A61M 25/02 128/877 |

(Continued)

FOREIGN PATENT DOCUMENTS

| | | | | | |
|---|---|---|---|---|---|
| EP | 2979623 A1 | * | 2/2016 | | |
| GB | 1131756 A | * | 10/1968 | ............. | A61F 5/442 |

*Primary Examiner* — Kevin C Sirmons
*Assistant Examiner* — William Carpenter
(74) *Attorney, Agent, or Firm* — Albert Bordas, P.A.

(57) ABSTRACT

A medical port assembly having a body assembly with a top wall, a bottom wall, first and second walls, and an interior wall. The body assembly further has an exterior wall and an interior adhesive wall. The interior adhesive wall has adhesive means. A permeable wall comprises a slit protected by an overlapping flap. The interior wall and the permeable wall define a cavity. A protective cover covers the interior adhesive wall and/or the cavity. The protective cover adheres to the adhesive. A feeding tube is positioned through the slit. The feeding tube has a distal end, an external retention ring, and at least one port defined as a feeding port, a medication port, or a fluid port. When not utilized, the feeding tube is stored within the cavity.

11 Claims, 3 Drawing Sheets

(56) References Cited

U.S. PATENT DOCUMENTS

| | | | | |
|---|---|---|---|---|
| 7,726,317 | B1* | 6/2010 | Garcia | A61F 15/008 |
| | | | | 128/887 |
| 2003/0041864 | A1* | 3/2003 | Altman | A61M 25/02 |
| | | | | 128/846 |
| 2004/0074501 | A1* | 4/2004 | Altman | A61F 15/008 |
| | | | | 128/852 |
| 2007/0049871 | A1* | 3/2007 | Fleischer | A61M 25/02 |
| | | | | 604/180 |
| 2010/0137805 | A1* | 6/2010 | Farchione | A61M 25/02 |
| | | | | 604/179 |
| 2011/0313360 | A1* | 12/2011 | Lin | A61M 39/02 |
| | | | | 604/179 |
| 2014/0061408 | A1* | 3/2014 | Heinecke | A61M 25/02 |
| | | | | 248/205.3 |
| 2014/0155973 | A1* | 6/2014 | Grigsby | A61N 1/0558 |
| | | | | 607/117 |
| 2014/0213981 | A1* | 7/2014 | Bockol | A61M 25/02 |
| | | | | 604/180 |
| 2014/0350474 | A1* | 11/2014 | Andreae | A61M 25/02 |
| | | | | 604/179 |

* cited by examiner

MEDICAL PORT ASSEMBLY

BACKGROUND OF THE INVENTION

1. Field of the Invention

The present invention relates to port assemblies, and more particularly, to medical port assemblies.

2. Description of the Related Art

A stoma is an incision into the human body to create an artificial opening to the exterior of the abdomen or the stomach. For gastrostomy, a feeding tube is connected to the stoma. Stomas are different in shape and size.

Several inventions for ostomy supplies have been developed in the past. However, Applicant is not aware of any medical port assemblies that facilitate and comfortably secure a feeding tube to the stoma, without affecting sensitive skin at the stoma opening.

SUMMARY OF THE INVENTION

The instant invention is a medical port assembly, comprising a body assembly having a top wall, a bottom wall, first and second walls, and an interior wall. The body assembly further comprises an exterior wall and an interior adhesive wall, which are connected to each other by the top wall, the bottom wall, and the first and second walls. In a preferred embodiment, the exterior wall and the interior adhesive wall are substantially parallel and spaced apart from each other. The body assembly is in a shape of a rectangle, circle, square, triangle, pentagon, hexagon, octagon, decagon, nonagon, trapezoid, parallelogram, rhombus, heptagon, star, crescent, oval, semicircle, cylinder, prism, or pyramid. The interior wall complements the shape of the body assembly. The body assembly is made of a soft yet resilient material. The soft yet resilient material is foam, sponge, porous rubber, or cellulose materials. The interior adhesive wall has adhesive means comprising an adhesive. The adhesive is a glue is acrylates, including methacrylates and epoxy diacrylates, or non-toxic glues.

A permeable wall is approximately flush with the exterior wall. The permeable wall comprises a slit protected by an overlapping flap. The interior wall and the permeable wall define a cavity. The permeable wall permits ambient air to enter and/or circulate though out the cavity. The permeable wall is made of a breathable and stretchable fabric. The permeable wall has a second cooperative shape and dimension to cover the cavity. The permeable wall may extend from the exterior wall.

A protective cover has a first cooperative shape and dimension to cover the interior adhesive wall and/or the cavity. The protective cover has first, second, third, and fourth edges. The protective cover adheres to the adhesive to protect the interior adhesive wall and prevents foreign matter from entering and/or accumulating within the cavity. The first, second, third, and fourth edges extend beyond the top wall, the bottom wall, and the first and second sidewalls to facilitate removal of the protective cover from the interior adhesive wall.

A feeding tube is positioned through the slit. The feeding tube has a distal end and an external retention ring positioned at a predetermined distance from the distal end. The proximal end of the feeding tube has at least one port defined as a feeding port, a medication port, and/or a fluid port.

It is therefore one of the main objects of the present invention to provide a medical port assembly that facilitates and comfortably secures the feeding tube to a stoma.

It is another object of this invention to provide a medical port assembly that can store the feeding tube when not being utilized.

It is another object of this invention to provide a medical port assembly that minimally affects sensitive skin at the stoma opening.

It is another object of this invention to provide a medical port assembly that supports an access to the stoma.

It is another object of this invention to provide a medical port assembly that comprises breathable, stretchable fabric.

It is another object of this invention to provide a medical port assembly comprising a protective cover to protect an adhesive area when not in use.

It is another object of this invention to provide a medical port assembly having an access opening protected by an overlapping tab when not in use.

It is another object of this invention to provide a medical port assembly that is volumetrically efficient for carrying, transporting, and storage.

It is another object of this invention to provide a medical port assembly that can be readily used without the need of any special tools.

It is another object of this invention to provide a medical port assembly, which is of a durable and reliable construction.

It is yet another object of this invention to provide such an assembly that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
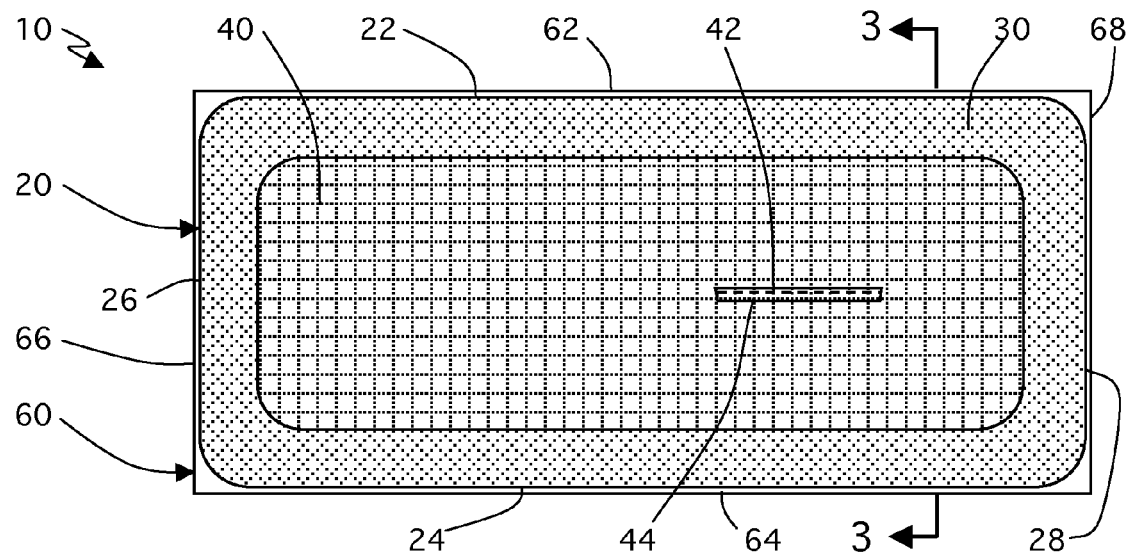
FIG. 1 represents a front view of a medical port assembly, object of the present invention.

Referring now to the drawings, the present invention is a medical port assembly and is generally referred to with numeral 10. It can be observed that it basically includes body assembly 20, permeable wall 40, and protective cover 60.

Figure 2:
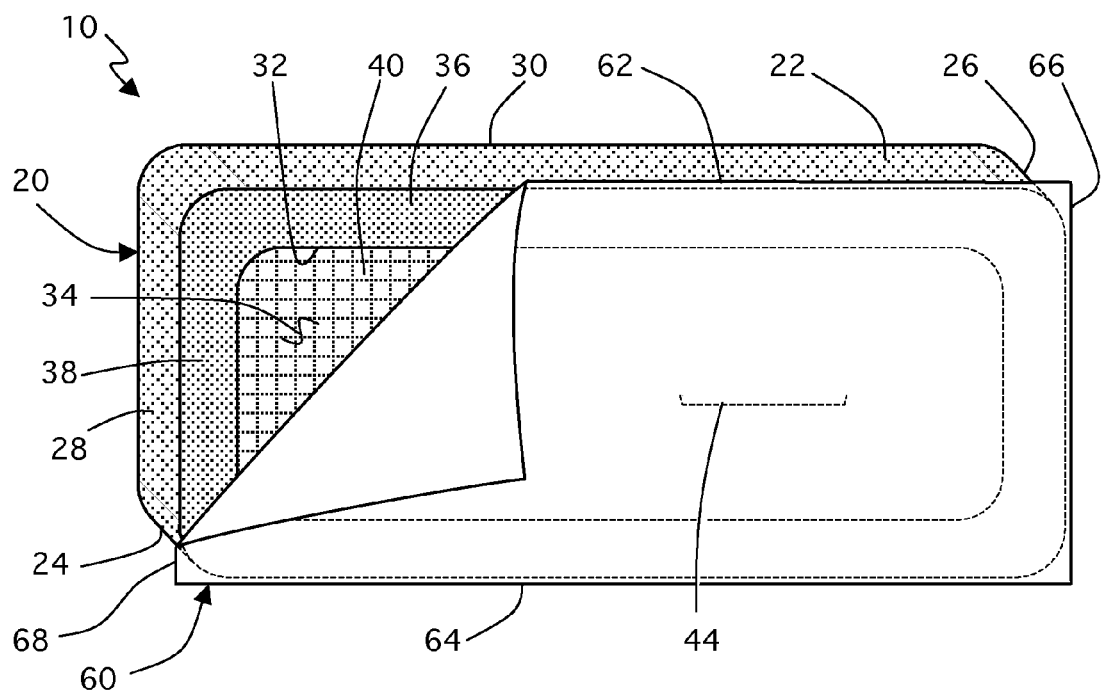
FIG. 2 is a rear view of the medical port assembly, showing a protective cover being removed from an interior adhesive wall.
Figure 3:
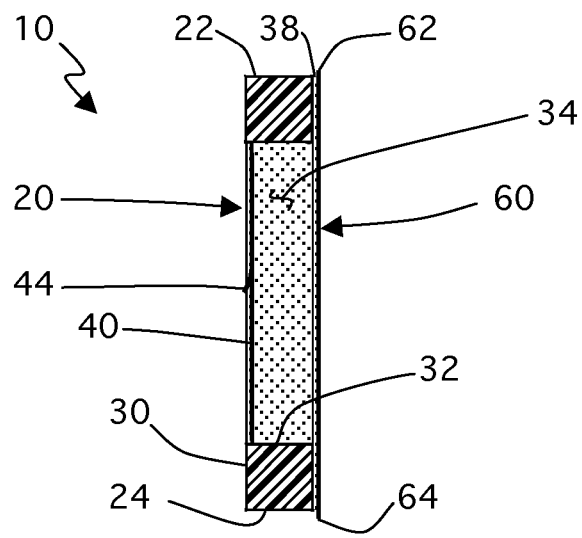
FIG. 3 is a side elevational view of the medical port assembly.

As seen in FIGS. 1, 2, and 3, body assembly 20 comprises top wall 22, bottom wall 24, sidewalls 26 and 28, and interior wall 32. Body assembly 20 further comprises exterior wall 30 and interior adhesive wall 36, which are connected to each other by top wall 22, bottom wall 24, and sidewalls 26 and 28. In a preferred embodiment, exterior wall 30 and interior adhesive wall 36 are substantially parallel and spaced apart from each other. Additionally in a preferred embodiment, body assembly 20 is rectangular in shape. However, body assembly 20 may be of any geometric shape, including but not limited to circle, square, triangle, pentagon, hexagon, octagon, decagon, nonagon, trapezoid, parallelogram, rhombus, heptagon, star, crescent, oval, semicircle, cylinder, prism, pyramid, etc. Interior wall 32 complements the shape of body assembly 20. In a preferred embodiment, body assembly 20 is made of a soft yet resilient material. Such a soft yet resilient material can be, but is not limited to foam, sponge, porous rubber, cellulose materials, or other materials having similar characteristics.

Permeable wall 40 is made of a breathable and stretchable fabric, and has a cooperative shape and dimension to cover cavity 34. In one embodiment, permeable wall 40 is approximately flush with exterior wall 30, whereby permeable wall 40 extends therefrom. Permeable wall 40 comprises slit 42 protected by overlapping flap 44 when not utilized. Interior wall 32 with permeable wall 40 define cavity 34. Cavity 34 is sufficiently large to store feeding tube 80, seen in FIG. 4, when not in use, whereby feeding tube 80 is folded, wrapped, coiled, or otherwise placed therein. Permeable wall 40 permits ambient air to enter and/or circulate though out cavity 34 to allow healing of a stoma and surrounding areas.

As seen in FIG. 2, interior adhesive wall 36 has adhesive means. Such adhesive means comprise adhesive 38. In a preferred embodiment, adhesive 38 is a glue including, but are not limited to, acrylates, including methacrylates and epoxy diacrylates, and non-toxic glues.

Protective cover 60, having edges 62, 64, 66, and 68, has a cooperative shape and dimension to cover interior adhesive wall 36 and cavity 34, whereby protective cover 60 adheres to adhesive 38. Protective cover 60 protects interior adhesive wall 36 and prevents foreign matter from entering and/or accumulating within cavity 34. Edges 62, 64, 66 and 68 extend beyond top wall 22, bottom wall 24, and sidewalls 26 and 28 respectively, to facilitate the removal of protective cover 60 from interior adhesive wall 36. In an alternate embodiment, protective cover 60 only covers interior adhesive wall 36, and not cavity 34.

Figure 4:
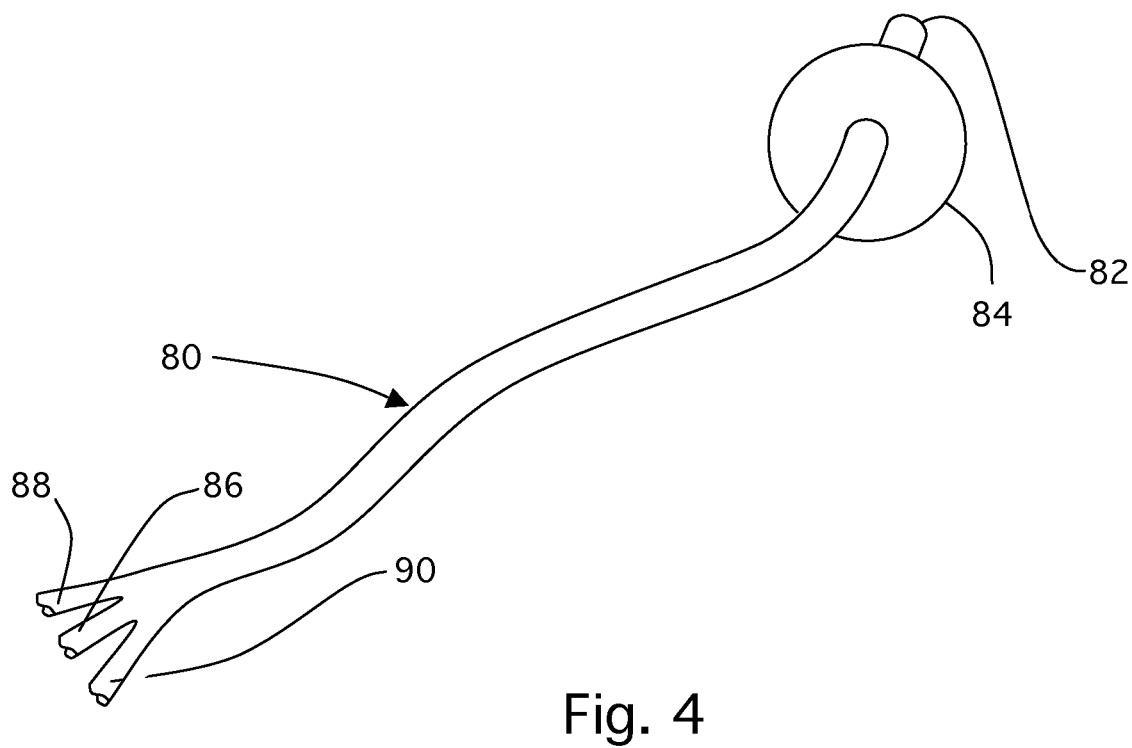
FIG. 4 is an isometric view of a feeding tube.

As seen in FIG. 4, a preferred embodiment for feeding tube 80 has distal end 82. External retention ring 84 is disposed at a predetermined distance from distal end 82. Feeding tube 80 has at least one port defined as a feeding port, a medication port, or a fluid port. As an example, a proximal end of feeding tube 80 has three ports, namely feeding port 86, medication port 88, and fluid port 90.

Figure 5:
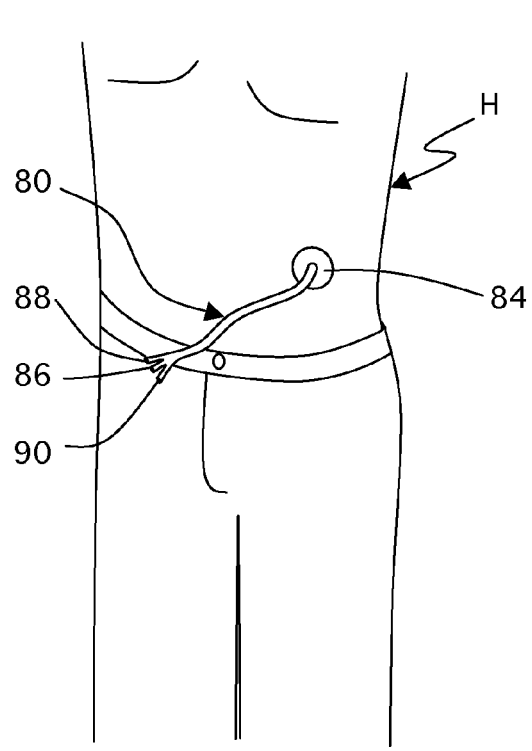
FIG. 5 is an isometric view of the feeding tube mounted to a stoma of a human.

As seen in FIG. 5, distal end 82 of feeding tube 80 (or other suitable medical supply) has been introduced into the stoma until external retention ring 84 covers the stoma opening of human H.

Figure 6:
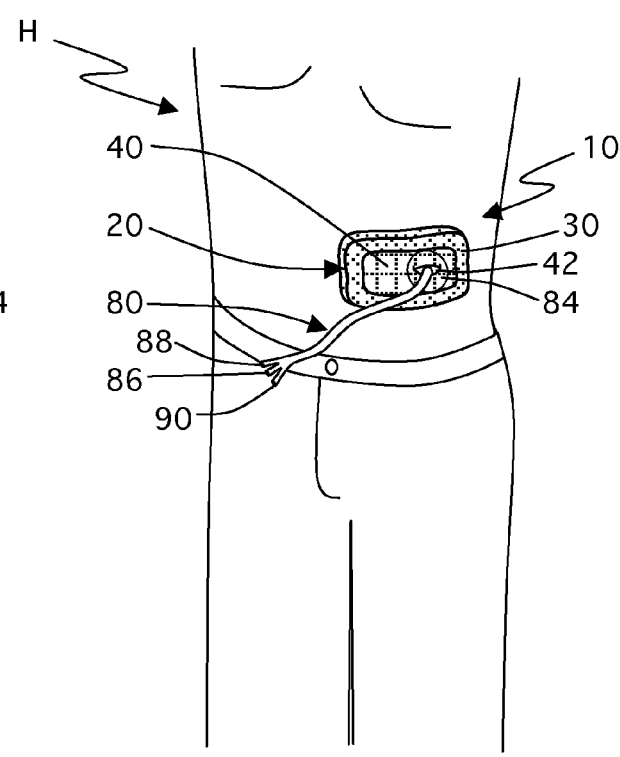
FIG. 6 is an isometric view of the feeding tube mounted to the stoma of the human, and showing the medical port assembly mounted and keeping the feeding tube in place.

As seen in FIG. 6, medical port assembly 10 is therefore used to support and protect an access to the stoma, preferably, while maintaining feeding tube 80 comfortably in place, whereby cavity 34 has a cooperative shape and dimension to house distal end 82, secured within the stoma, and external retention ring 84 when feeding tube 80 is in use.

To place medical port assembly 10 thereon, a person removes protective cover 60 from body assembly 20. Overlapping flap 44 is pushed aside to expose slit 42 and the proximal end of feeding tube 80 is passed through slit 42. Interior adhesive wall 36 is pressed around the stoma, housing external retention ring 84 within cavity 34. Optionally, body assembly 20 may be further secured with medical adhesive tape, not seen. When feeding tube 80 is not being utilized, it may be folded, wrapped, coiled, or otherwise placed within cavity 34. By protecting feeding tube 80 while mounted to the stoma and stored within cavity 34, a user can wear articles of clothing to cover areas over instant invention 10.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A medical port assembly, comprising:
   A) a body assembly comprising a top wall, a bottom wall, first and second walls, and an interior wall, said body assembly further comprises an exterior wall and an interior adhesive wall, which are connected to each other by said top wall, said bottom wall, and said first and second walls, said body assembly is made of a soft yet resilient material, and said soft yet resilient material is foam, sponge, porous rubber, or cellulose materials, said interior adhesive wall has adhesive means comprising an adhesive, said adhesive is a glue including acrylates, methacrylates and epoxy diacrylates, or non-toxic glues;
   B) a permeable wall approximately flush with said exterior wall, said permeable wall comprises a slit protected by an overlapping flap, said overlapping flap extends from said permeable wall and extends an entire length of said slit from one side of said slit, said interior wall and said permeable wall define a cavity, said permeable wall permits ambient air to enter and/or circulate though out said cavity, a feeding tube is positioned through said slit, whereby said overlapping flap is pushed aside to expose said slit and a proximal end of said feeding tube is passed through said slit, and when said feeding tube is not being utilized, it may be folded, wrapped, coiled, or otherwise placed within said cavity, whereby said permeable wall and said cavity make up a majority area as compared to said body assembly, said feeding tube has a distal end and an external retention ring positioned at a predetermined distance from said distal end; and
   C) a protective cover having a first cooperative shape and dimension to cover said interior adhesive wall.

2. The medical port assembly set forth in claim 1, further characterized in that said exterior wall and said interior adhesive wall are substantially parallel and spaced apart from each other.

3. The medical port assembly set forth in claim 1, further characterized in that said body assembly is in a shape of a rectangle, circle, square, triangle, pentagon, hexagon, octagon, decagon, nonagon, trapezoid, parallelogram, rhombus, heptagon, star, crescent, oval, semicircle, cylinder, prism, or pyramid.

4. The medical port assembly set forth in claim 3, further characterized in that said interior wall complements said shape of said body assembly.

5. The medical port assembly set forth in claim 1, further characterized in that said permeable wall is made of a breathable and stretchable fabric.

6. The medical port assembly set forth in claim 1, further characterized in that said permeable wall has a second cooperative shape and dimension to cover said cavity.

7. The medical port assembly set forth in claim 1, further characterized in that said permeable wall extends from said exterior wall.

8. The medical port assembly set forth in claim 1, further characterized in that said protective cover has first, second, third, and fourth edges, said protective cover adheres to said adhesive to protect said interior adhesive wall and prevents foreign matter from entering and/or accumulating within said cavity.

9. The medical port assembly set forth in claim 8, further characterized in that said first, second, third, and fourth edges extend beyond said top wall, said bottom wall, and said first and second sidewalls to facilitate removal of said protective cover from said interior adhesive wall.

10. The medical port assembly set forth in claim 1, further characterized in that said proximal end of said feeding tube has at least one port defined as a feeding port, a medication port, or a fluid port.

11. The medical port assembly set forth in claim 1, further characterized in that said protective cover also covers said cavity.

\* \* \* \* \*